United States Patent [19]

Heck et al.

[11] 4,229,261
[45] Oct. 21, 1980

[54] PROCESS FOR SEPARATING WATER FROM ORGANIC MULTIPLE COMPONENT MIXTURES BY DISTILLATION

[75] Inventors: Günter Heck, Hofheim; Günter Roscher; Rudolf Donth, both of Kelkheim, all of Fed. Rep. of Germany

[73] Assignee: Hoechst Aktiengesellschaft, Frankfurt am Main, Fed. Rep. of Germany

[21] Appl. No.: 971,900

[22] Filed: Dec. 21, 1978

Related U.S. Application Data

[63] Continuation of Ser. No. 487,741, Jul. 11, 1974, abandoned.

[30] Foreign Application Priority Data

Jul. 13, 1973 [DE]  Fed. Rep. of Germany ....... 2335673

[51] Int. Cl.² .......................... B01D 3/36; C07B 51/42
[52] U.S. Cl. ........................................ 203/14; 203/16; 203/98; 562/608; 560/248
[58] Field of Search ...................... 203/14, 16, 15, 18, 203/98, 60, 95, 96, 97; 562/248, 608

[56] References Cited

U.S. PATENT DOCUMENTS

| | | | |
|---|---|---|---|
| 2,048,178 | 7/1936 | Carney | 203/18 |
| 2,729,600 | 1/1956 | Beach | 203/71 |
| 2,859,154 | 11/1958 | Othmer | 203/35 |
| 3,052,610 | 9/1962 | Akaboshi et al. | 203/16 |
| 3,431,181 | 3/1969 | Bouniot | 203/18 |
| 3,438,870 | 4/1969 | Roscher et al. | 203/14 |
| 3,692,636 | 9/1972 | Huguet | 203/71 |

Primary Examiner—Wilbur L. Bascomb, Jr.
Attorney, Agent, or Firm—Curtis, Morris & Safford

[57] ABSTRACT

Water is separated by distillation from organic multiple component mixtures containing at least one component partly miscible with water. The component miscible with water is distilled azeotropically with the water contained in the mixture, the distillate is separated into water and a zeotrope forming agent and the latter is recycled to the distilling column. In the recycling process, one part of the azeotrope forming agent is conducted to the top of the column and the other part is fed into the column at the feed mixture inlet or at a location thereunder.

4 Claims, 1 Drawing Figure

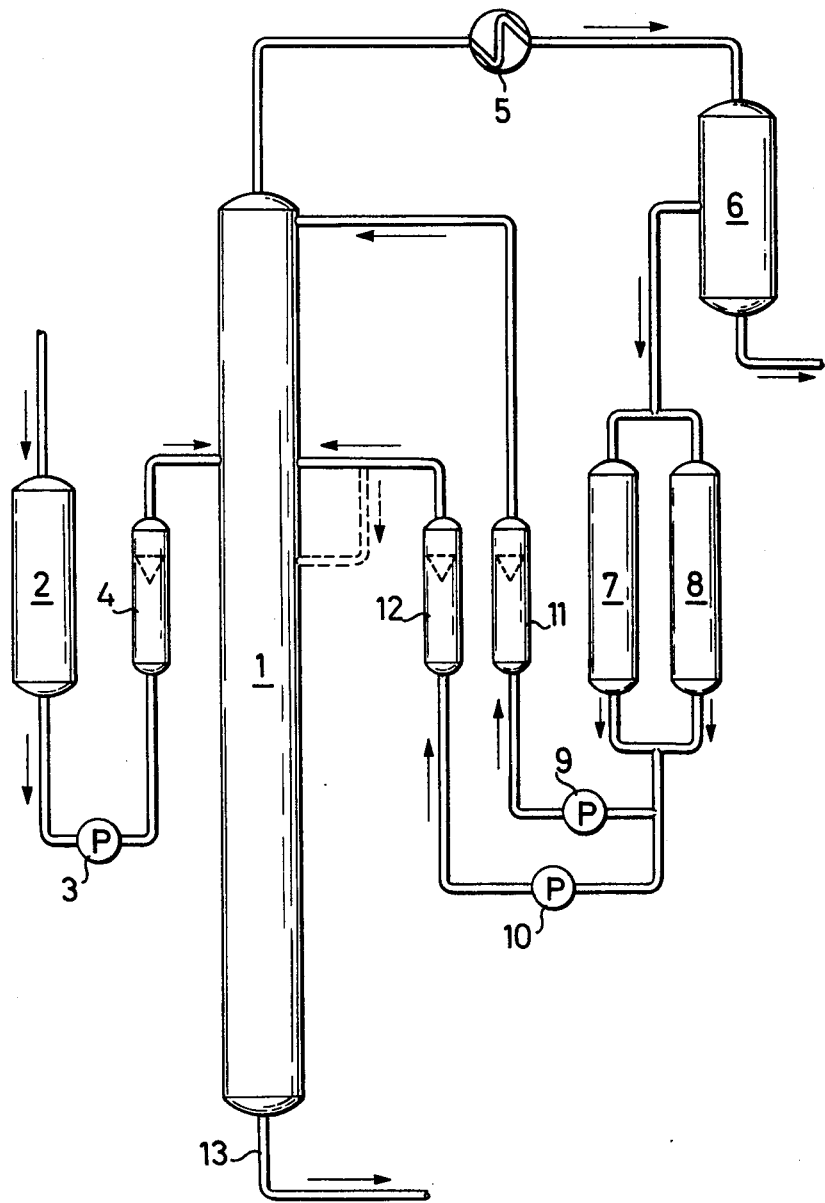

PROCESS FOR SEPARATING WATER FROM ORGANIC MULTIPLE COMPONENT MIXTURES BY DISTILLATION

This is a continuation, of application Ser. No. 487,741, filed July 11, 1974 now abandoned.

The present invention provides a process for separating water by distillation from organic multiple component mixtures containing at least one component partly miscible with water.

In a series of technical processes water-containing organic multiple component mixtures are obtained, wherefrom water must be removed by distillation. The separation can be carried out in simple manner, if the water is obtained without an additional expenditure for the separation in the form of a distillate or bottom product without residual content of organic components, as, for example, in the dehydration of glycerine (water head product) or methanol (water bottom product). In general, the conditions for separating are more complicated owing to the fact that binary or ternary water-containing boiling mixtures are obtained. For this reason, for eliminating the water by distillation, components are added in general, which are nonmiscible or little miscible with water and form with water an azeotrope, so as to produce a phase separation of the distillate into aqueous and an organic phase. The aqueous phase is separated and the azeotrope forming organic phase is reconducted to the distilling column. The organic azeotrope forming agent can be added to the mixture as foreign component or already be present in the mixture to be worked up. The azeotropic dehydation requires a high energie expenditure if the water-content of the distilling water-entrainer mixture is low, because in this case a great quantity of organic azeotrope forming agents must be evaporated for eliminating the water. The economy of the azeotropic dehydration consequently depends on one hand, on the water-content of the distilling vapor phase and on the other hand on the solubility of water in the organic phase after condensation and phase separation, because the quantity of water dissolved in the organic azeotrope forming component is recycled to the distilling column. The consumption of energie depends on the quantity of water which can be discharged per unit of weight of the total distillate, resulting from the difference between the quantity of water in the total distillate and the quantity of water which is recycled to the distilling column with the organic phase. If the azeotrope forming component for the water to be discharged is already present in the mixture, the azeotropic dehydration is generally carried out as follows: The mixture is continuously fed to the distilling column, the aqueous phase is drawn off the two-phase distillate and the organic phase is recycled to the top of the column or into the column between the top and the inlet of the feed mixture in order to from an azeotrope again. (Cf. R. Billet, "Grundlagen der thermischen Flüssigkeitszerlegung", B. I. Hochschultaschenbücher, 1962, page 142). The water phase is then drawn off in the form of a distillate. The water-free or almost water-free mixture constitutes the bottom product. The technical mixtures, wherefrom water must be separated, in general still contain components miscible with water, such as carboxylic acids having less than 5 carbon atoms. It is therefore necessary that the distilling column has a layout such that the water-soluble component cannot pass into the distillate, where it would impair the formation of two phases. In order that this does not happen the azeotrope forming agent refluxing from the phase separator is introduced at the top of the column. The water-soluble component is rectified between the top and the inlet for the fed mixture. The total distillate obtained as described above contains a quantity of water substantially smaller than the theoretical water-content of the azeotrope of the specific water-containing entrainer. Methods for increasing the content of water of the distillate therefore are of technical importance because they reduce the energy expenditure for separating the water.

It has now been found that the water-content of the distillate can be materially improved surprisingly by dividing the organic phase, which hitherto has been recycled entirely to the top of the column after phase separation of the distillate, into a part which is recycled to the top of the column and a part which is recycled into the distilling column together with the water-containing multiple component feed mixture or at a location below the inlet for the multiple component feed mixture.

The present invention consequently provides a process for separating water by distillation from organic multiple component mixtures containing one component partly miscible with water, by azeotropic distillation of the aforesaid component with the water contained therein, by phase separation of the distillate and by recycling of the azeotrope forming agent into the column, which comprises dividing the organic phase prior to being recycled into the column, recycling one part of the aforesaid phase into the column at the top of the column and the other part via the inlet of the said mixture or at a location below the said inlet.

The following description and the examples illustrate the invention. The invention is further illustrated diagrammatically by way of example in the accompanying flow sheet.

In the following examples the mixture is worked up in a glass bubble cap plate column (1) having 55 plates and an inner diameter of 50 mm. The feed-stock is pumped from the storage and balance vessel (2) to the $40^{th}$ plate of the column by pump (3) via the flow meter (4). The distillate is liquified in the condenser (5) cooled with water and collected in the separator (6), where the separation into organic and aqueous phase takes place. The aqueous phase is drawn off and the organic phase is passed to two alternately operated balance vessels (7) and (8). The organic distillate is recycled from the balance vessels (7 and 8) to the distilling column by pumps (9 and 10) i.e. to the top of the column by pump (9) via flow meter (11) and to the $40^{th}$ plate of the column by the pump (10) via flow meter (12). The bottom product is drawn off the column (1) through conduit (13).

EXAMPLE 1

Dehydration of a mixture of vinyl acetate, acetic acid and water. The feed-stock consits of 53% by weight of acetic acid, 12% by weight of water and 35% by weight of vinyl acetate.

(a) without reflux division 516 g/h of the mixture are introduced into the column. The distillate is separated in the phase separator (6) into an aqueous phase, which is drawn off, and an organic phase, which is recycled without being divided to the top of column (1) over recipients (7) and (8) over the flow meter (11) by means of the pump (9). After adjusting constant test conditions, 1030 g of organic phase and 41 g of aqueous phase are obtained per hour in the separator at a head temperature of 68.5° C. The water discharge calculated on the total distillate amounts to 3.8%.

(b) with reflux division 520 g per hour of the mixture mentioned above are introduced into the column. The organic phase separated in the phase separator (6) and recycled into the column over the recipients (7) and (8) is divided. 4/5 of the organic reflux are recycled into the column at the inlet for the mixture by pump (10) via flow meter (12), 1/5 of the organic reflux are recycled to the top of the column by pump (9) via flow meter (11). After adjusting constant test conditions, 940 g of organic phase and 55 g of water phase are obtained per hour at a head temperature of 67° C. The water discharge calculated on the total distillate amounts to 5.5%. Owing to the reflux division an increase of the water discharge of about 30% can be obtained with the same energy expenditure.

EXAMPLE 2

Dehydration of a mixture of acetic acid, ethyl acetate and water. The feed-stock consists of 45% by weight of acetic acid, 20% by weight of water and 35% by weight of ethyl acetate.

(a) without reflux division 500 g/h of the mixture are introduced into the column, the test arrangement being as in example 1 (a). 1010 g of organic phase and 57 g of water phase are obtained per hour at a head temperature of 74° C. The water discharge calculated on the total distillate, ignoring the ethyl acetate dissolved in the water phase, is 5.2%.

(b) with reflux division 510 g/h of the mixture are introduced into the column, the test arrangement being as in example 1 (b). 1020 g of organic phase and 85 g of aqueous phase are obtained per hour at a head temperature of 72° C. The water discharge calculated on the total distillate, ignoring the ethyl acetate dissolved in the aqueous phase, is 7.7%.

Owing to the reflux division an increase of the water discharge of 32% can be obtained with the same energy expenditure.

What is claimed is:

1. A distillation process for the removal of water from organic multiple component mixtures containing water and consisting essentially of carboxylic acids having less than 5 carbon atoms and esters thereof, at least one of said organic components being partly miscible with water and being an azeotrope forming agent, comprising the steps of: introducing said organic multiple component mixture containing water into an inlet of a distillation column, azeotropically distilling overhead the water and the partly miscible azeotrope forming agent in said distillation column; condensing the resultant azeotropic distillate and separating the condensate into a water layer which is removed and an azeotrope forming agent layer; separating substantially all of the azeotrope forming agent layer into two parts and recycling one part to the top of the distillation column and the other part to the column at a point at or below the mixture inlet; and removing said organic multiple component mixture, free or almost free of water as a bottoms product.

2. The process of claim 1 wherein the organic multiple component mixture consists essentially of acetic acid and vinyl acetate.

3. The process of claim 1 wherein the organic multiple component mixture consists essentially of acetic acid and ethyl acetate.

4. The process of claim 1 wherein about four-fifths of the azeotrope forming agent is recycled into the column at the inlet for the feed mixture and about one-fifth of the azeotrope forming agent is recycled to the top of the distillation column.

* * * * *